United States Patent [19]

Nebolon

[11] Patent Number: 5,454,383
[45] Date of Patent: Oct. 3, 1995

[54] METHOD FOR PREFITTING AN ORTHOTIC MEMBER TO THE BODY

[75] Inventor: Joseph F. Nebolon, Del Mar, Calif.

[73] Assignee: Smith & Nephew Donjoy, Inc., Carlsbad, Calif.

[21] Appl. No.: 87,997

[22] Filed: Jul. 2, 1993

[51] Int. Cl.⁶ .............................. A61F 2/78; G06F 15/42; B29C 33/40
[52] U.S. Cl. ............................ 128/898; 602/6; 264/222; 364/413.13; 623/901
[58] Field of Search ................... 128/898; 602/5, 602/6, 16, 20, 23, 26, 39; 264/222, 223, DIG. 30; 364/413.13–413.16, 413.19; 623/901

[56] References Cited

U.S. PATENT DOCUMENTS

| | | |
|---|---|---|
| 2,687,129 | 8/1954 | Talkish . |
| 3,711,350 | 1/1973 | Witzel, III . |
| 3,934,583 | 1/1976 | Hollingshead et al. . |
| 4,071,914 | 2/1978 | Silverman . |
| 4,663,720 | 5/1987 | Duret et al. . |
| 4,722,056 | 1/1988 | Roberts et al. . |
| 4,742,464 | 5/1988 | Duret et al. . |
| 4,783,293 | 11/1988 | Wellershaus et al. ............. 264/222 X |
| 4,821,200 | 4/1989 | Oberg . |
| 4,972,351 | 11/1990 | Reger et al. ...................... 264/222 X |
| 5,211,894 | 5/1993 | Groh et al. ....................... 264/222 X |
| 5,258,036 | 11/1993 | Edenbaum et al. ................ 264/222 X |

FOREIGN PATENT DOCUMENTS

| | | | |
|---|---|---|---|
| 2591473 | 12/1985 | France | .............. A61F 5/03 |
| 9102496 | 3/1991 | WIPO | .................. 623/901 |
| 9107139 | 5/1991 | WIPO | .................. 623/901 |
| WO93/05735 | 4/1993 | WIPO | .............. A61F 5/02 |

*Primary Examiner*—Linda C. M. Dvorak
*Attorney, Agent, or Firm*—Rodney F. Brown

[57] ABSTRACT

A method is provided for prefitting a stiffened member to a curved body having a geometry approximatable by a cone. Two points are initially selected on the surface of the body which also lie on two different planes passing through the body, such that the intersection of the surface and the planes defines two closed curves. A cone is approximated based on parameters relating to the curves and the selected points. A three-dimensional pattern of a stiffened member is then superimposed onto the conical surface at a modeling position corresponding to the desired placement position of the member on the body. The geometry and dimensions of the pattern are mathematically specified relative to the conical surface and the specifications provide a model for fabricating the prefitted stiffened member.

25 Claims, 4 Drawing Sheets

METHOD FOR PREFITTING AN ORTHOTIC MEMBER TO THE BODY

TECHNICAL FIELD

The present invention relates generally to orthotics, and more particularly to a method for prefitting a stiffened orthopedic brace component to a curved surface of the body.

BACKGROUND OF THE INVENTION

The proper fit of an orthotic device to the body of a patient is critical to performance of the device, as well as to the comfort of the patient. The fit of common orthotic devices, such as orthopedic braces for joint stabilization, is often approximated by offering a matrix of several sizes, across the entire size range. For example, a typical size matrix is small, medium, and large. The contours of the human body, however, are not always uniform and symmetrical, thereby rendering the standardization of properly fitting size matrices for orthotic devices problematic.

The problem is particularly acute when attempting to fit the human body with off-the-shelf orthotic devices having support components fabricated from relatively stiff materials, such as metals or rigid plastics. Because these components lack the ability to conform to the curves of the body contours, they are often preformed to have a generalized curved configuration that is intended to approximate the shape of the body and provide a close fit thereto. Nevertheless, it has been found that the body contours often have irregularities that the generalized curves of preformed orthotic devices do not adequately approximate.

As an alternative to standardized size matrices, orthotic devices can be customized for a more proper fit. Custom fitting, however, requires a large number of measurements of individual body dimensions rendering custom fitting and custom fabrication processes time-consuming and costly.

Accordingly, it is an object of the present invention to provide a systematic method for prefitting a stiffened member to a curved surface that is applicable to both standardized sizing and custom fitting of the member to the surface. It is a particular object of the present invention to provide a systematic method for prefitting a stiffened orthotic device to a curved surface of the human body.

It is another object of the present invention to provide a systematic method for prefitting the orthotic device to the human body that is adaptable to the oftentimes irregular and complex contours of the body. It is still another object of the present invention to provide a systematic method for prefitting the orthotic device to the human body that integrates relatively complex curves into the preformed device closely approximating the contours of the body. It is yet another object of the present invention to provide a systematic method for prefitting a substantially customized or off-the-shelf orthotic device to the human body that requires relatively few preliminary measurements of the patient being prefitted with the device. It is an alternate object of the present invention to provide a systematic method for prefitting an off-the-shelf orthotic device to the human body that requires no preliminary measurements of the patient being prefitted with the device, but bases the fit on a statistical survey of body measurements from a population pool.

It is another object of the present invention to provide a systematic method for prefitting the orthotic device to the human body that establishes a relatively accurate, yet uniform and simple, analytical model of a human body to which a pattern of the device can be fitted. It is a further object of the present invention wherein such a pattern establishes corresponding fabrication parameters used to create the prefitted orthotic device. In accordance with the following disclosure, the present invention is shown to satisfy the above-recited objectives and others as will be apparent to the skilled artisan.

SUMMARY OF THE INVENTION

The present invention is generally a method for prefitting a stiffened member to a curved body having a geometry approximatable by a cone. Specifically, the method encompasses prefitting a stiffened orthotic member, such as a rigid or semi-rigid orthopedic brace component, to a curved, but oftentimes irregular, surface of a substantially tapered human body section.

In accordance with the present method, two points are initially selected on the curved surface of a body to which the practitioner desires to prefit a stiffened member. The points are selected to lie on two different planes passing through the body that are spaced a longitudinal distance apart from one another, such that the intersection of the curved body surface and the two planes defines two distinct closed curves.

A cone having a defined conical surface approximating the curved body surface is derived based on the longitudinal distance and the two curves. A three-dimensional pattern of the stiffened member is then superimposed onto the conical surface at a modeling position corresponding to the desired placement position of the member on the curved body surface. Finally, the geometry and dimensions of the pattern are mathematically specified relative to the defined conical surface by analytical methods. The mathematical specifications of the pattern subsequently provide a model for fabricating a stiffened member prefitted to the curved surface of the body at the desired placement position.

The present invention includes two specific embodiments. One embodiment applies to cases where the peripheral curves defined by the intersection of the two planes and the curved body surface are approximatable by two circles. Another embodiment applies to cases where the peripheral curves are more closely approximatable by two ellipses.

In accordance with a first embodiment, the two peripheral curves are defined in the manner recited above and two circles are approximated therefrom. Since a circle can be completely defined by a single parameter selected from a group of quantifiable parameters including the radius, diameter or circumference, the value of at least one, and preferably only one, such circle-defining parameter is determined for each approximated circle.

The values of the circle-defining parameters and the value of the longitudinal distance between the two selected points together define a circular cone having a conical surface that approximates the curved surface of the body. Thereafter, a pattern is superimposed onto the conical surface in substantially the same manner as recited above, providing a basis for fabricating a stiffened member prefitted to the curved surface of the body.

In accordance with a second embodiment of the invention, the two peripheral curves are again defined in the manner recited above. Since the peripheral curves, however, more closely resemble ellipses, two ellipses are approximated from the curves. Values are then determined for a number of quantifiable parameters sufficient to define each ellipse. A preferred set of ellipse-defining parameters is the length of the major axis and the length of the minor axis for each ellipse.

The values of the ellipse-defining parameters and the value of the longitudinal distance between the two selected points are combined to define an elliptical cone having a conical surface that approximates the curved surface of the body. As above, a prefitted stiffened member may then be fabricated on the basis of a pattern superimposed onto the conical surface.

The present invention will be further understood from the accompanying description taken in conjunction with the accompanying drawings, in which similar reference characters refer to similar parts.

DESCRIPTION OF PREFERRED EMBODIMENTS

Figure 1:
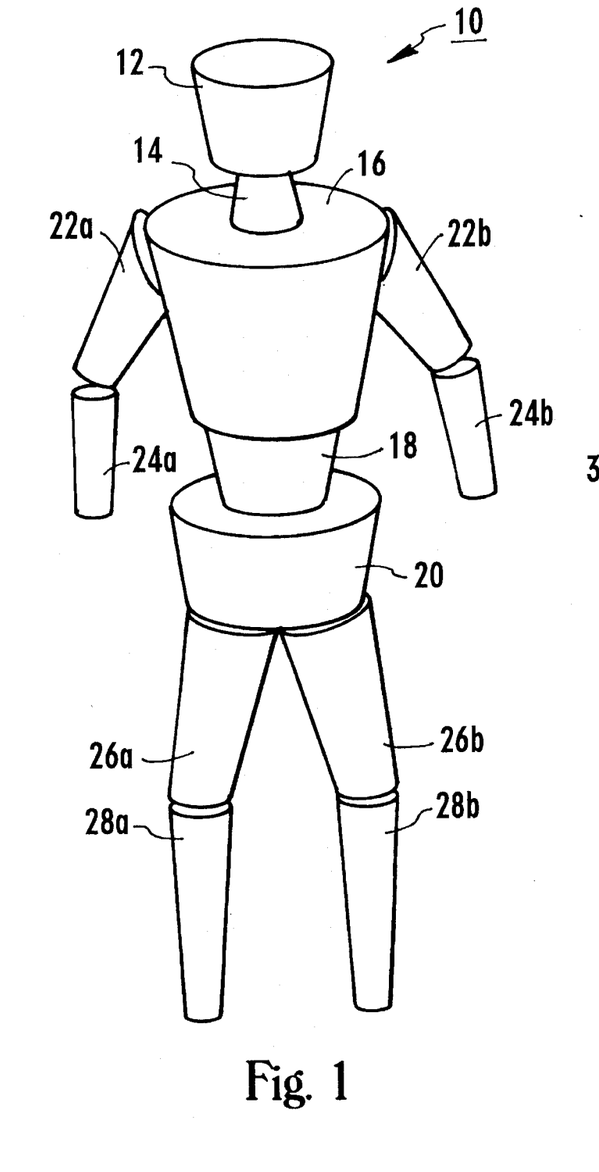
FIG. 1 conceptually depicts a human body modeled by a series of cones.

The present invention provides a method for prefitting an orthotic device to the curved surface of a desired section of the human body, typically having an at least somewhat uneven or asymmetrical, tapered shape that can, nevertheless, be approximated by a conical surface of a cone, and preferably an elliptical or circular cone. FIG. 1 is a model of a human body designated 10, wherein the generally tapered body sections are modeled by cones. As the term is used herein, "cone" refers to whole cones and to portions of cones formed by passing a plane through a cone, thus, for example, dividing the cone into a base-containing portion and an apex-containing portion.

As shown in FIG. 1, the human head is modeled by a cone 12, and the neck by a cone 14. The trunk sections, including the chest or thoracic section, the abdominal section, and the pelvic section, are modeled by cones 16, 18, and 20, respectively. The limb sections, including the upper arms, the lower arms or forearms, the upper legs or thighs, and the lower legs, are modeled by cones 22a and 22b, 24a and 24b, 26a and 26b, and 28a and 28b, respectively.

The present method has particular utility to prefitting a stiffened frame of an orthopedic brace to the curved surface of a body section adjacent to a body joint being supported by the brace. More specifically, the method has utility to prefitting the cuff component of the frame to the curved body surface above or below the joint being supported thereby, such that the cuff effectively and comfortably stabilizes the brace at the points of engagement between the cuff and body.

The present method can, for example, be applied to prefitting a thigh or calf cuff of a conventional knee brace, such as disclosed in U.S. Pat. No. 4,697,583 incorporated herein by reference, to the leg sections of a patient. By way of other examples, the present method can be applied to prefitting the cuffs of a conventional shoulder brace to the arm and torso sections of a patient, and to prefitting the cuffs of a conventional hip brace to the leg and torso sections of a patient.

For purposes of illustration, the present method is described hereafter in the context of prefitting a stiffened thigh cuff, functioning as a support component of a knee brace, to the thigh of a patient. It is understood by the skilled artisan, however, that the method disclosed herein has broader applications to prefitting substantially any stiffened orthotic member to a curved surface of a human body section approximatable by the conical surface of a circular or elliptical cone. It is further apparent to the skilled artisan that the present method has generalized applications to prefitting substantially any stiffened member to the curved surface of a body approximatable by a conical surface of a circular or elliptical cone.

Figure 2:
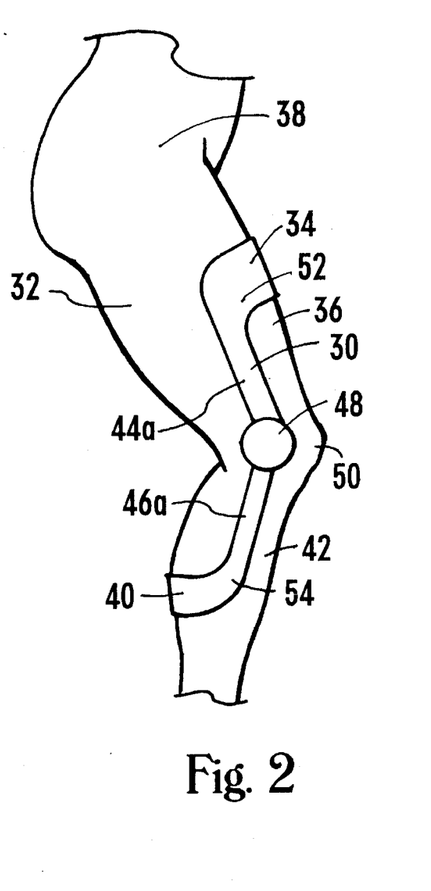
FIG. 2 is a perspective view of a conventional knee brace positioned on the leg of a patient.

With reference to FIG. 2, the support components of a typical knee brace 30 are shown in position on the leg 32 of a patient. A stiffened thigh cuff 34 engages the upper leg section 36 below the hip joint 38 and supports the brace 30 thereagainst. A stiffened calf cuff 40 engages the lower leg section 42 and further supports the brace 30 thereagainst. The thigh cuff 34 is rotatably connected to the calf cuff 40 by a rigid upper arm 44a and a rigid lower arm 46a, and a rotatable hinge 48 adjacent to the knee joint 50. An identical pair of upper and lower arms and a hinge (not shown) connect the thigh cuff 34 with the calf cuff 40 on the opposite side of the leg 32. Flexible straps (not shown) are also commonly provided about the brace 30 and leg 32 to secure the brace 30 to the leg 32.

In the present embodiment, both upper arms of brace 30 (only 44a is shown herein) are integrally formed with the thigh cuff 34 to provide a single upper leg support member 52. Thus, it is preferable to prefit the entire support member 52 to the upper leg section 36 in the manner of the present method incident to prefitting the thigh cuff 34 to the upper leg section 36. Likewise, both lower arms (only 46a is shown herein) and the calf cuff 40 integrally form a lower leg support member 54 that is preferably prefitted to the lower leg section 42 in its entirety incident to prefitting the calf cuff 40 to the lower leg section 42.

The term "stiffened" refers to the degree of flexibility and elasticity of a material. As defined herein, a "stiffened" member ranges in flexibility and elasticity from a rigid material to a semi-rigid material. A rigid material is substantially inflexible and inelastic, whereas a semi-rigid material is resistant to flexion, yet has some limited flexibility, particularly in the lateral direction. In addition, a semi-rigid material is elastic to the extent that the material returns to its original configuration after limited flexion.

Figure 3:
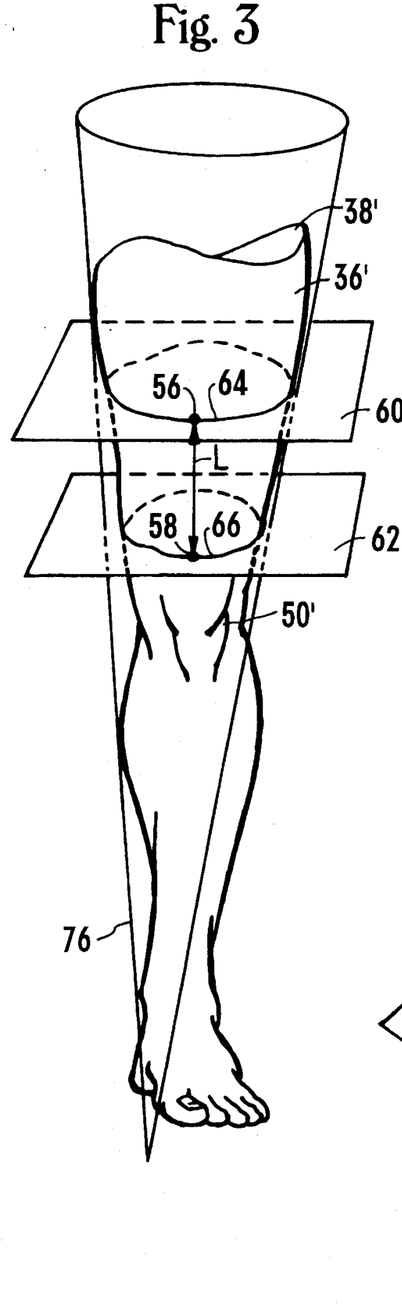
FIG. 3 is a perspective view of a leg to be prefitted with a thigh cuff and having a conical surface superimposed over the upper leg, wherein the conical surface is approximated in accordance with the present invention.

Referring now to FIG. 3, prefitting an upper leg support member of the type shown in FIG. 2, including a thigh cuff, is initiated in accordance with the present method by selecting two points 56 and 58 on the surface of the upper leg section 36' having a longitudinal distance L therebetween. The longitudinal distance L can be arbitrarily selected, to the extent it has some value other than zero. Thus, points 56 and 58 can be selected substantially anywhere on the surface of the upper leg section 36' between the hip joint 38' and the knee joint 50', inclusive, subject to the above-recited limitation.

Each point 56, 58 is contained within a discrete plane 60, 62, respectively, passing through the upper leg section 36'. The planes 60, 62 are preferably substantially parallel to one another, and more preferably perpendicular to the longitudinal axis of the upper leg section 36', i e cross-sectional relative to the upper leg section 36'. The intersection of each plane 60, 62 and the surface of the upper leg section 36' defines a pair of closed peripheral curves 64, 66 with the respective points 56, 58 lying thereon.

Figure 4A:
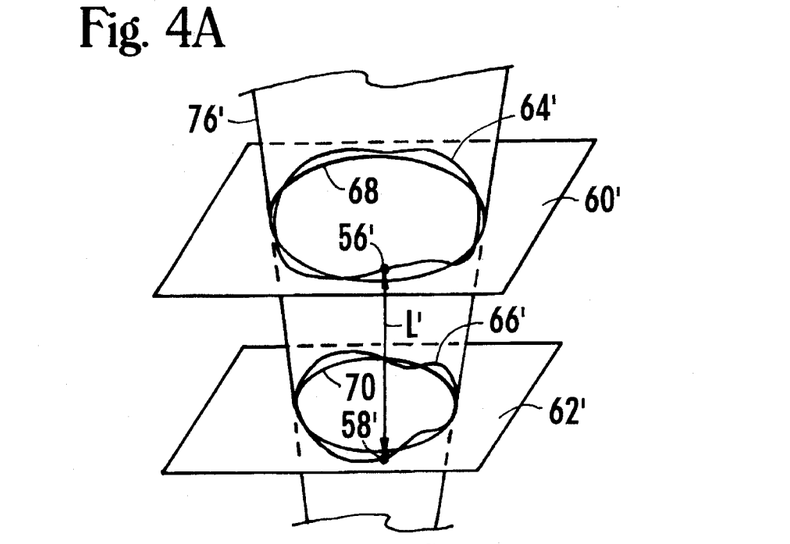
FIG. 4A is a perspective view of two planes, each having a selected point lying thereon and further having a circle approximated thereon in accordance with the present invention.

Insofar as the contours of the upper leg section 36' are somewhat irregular, the curves 64, 66 are not exact geometric shapes. Where the peripheral curves 64' and 66' resemble circles, however, as shown in FIG. 4A, a pair of circles 68 and 70 lying on the planes 60' and 62' that contain the points 56' and 58', respectively, are approximated therefrom, such as by known analytical methods. Where the peripheral curves 64" and 66" resemble ellipses, as shown in FIG. 4B, a pair of ellipses 72 and 74 lying on the planes 60" and 62" that contain the points 56" and 58", respectively, are approximated therefrom, such as by known analytical methods.

With reference to FIG. 4A, each circle 68, 70 is defined by its geometrical parameters. To minimize the number of required leg measurements, it is preferable to select a circle-defining parameter which alone can uniquely define each circle 68 or 70. Such preferred circle-defining parameters include the radius, diameter and circumference. Accordingly, a measurement of the selected circle-defining parameter for each circle 68, 70 is obtained from the leg and synthesized with a measurement obtained from the leg for the longitudinal length L' between points 56' and 58' to define a circular cone 76' shown in partial outline.

Figure 4B:
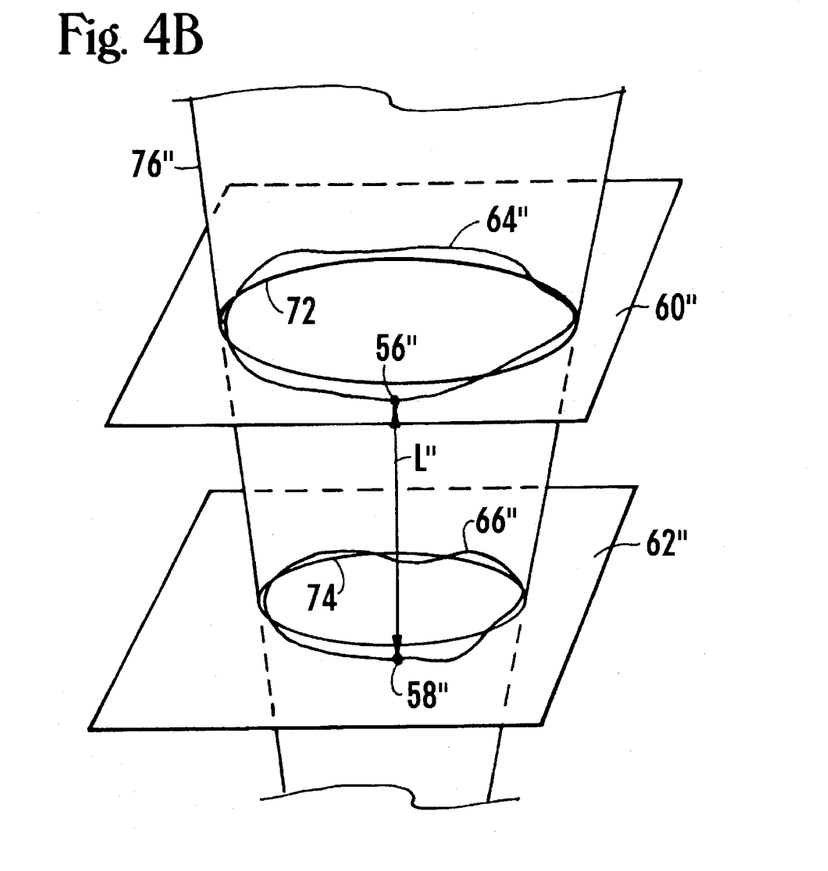
FIG. 4B is a perspective view of two planes, each having a selected point lying thereon and further having an ellipse approximated thereon in accordance with the present invention.

Similarly, with reference to FIG. 4B, each ellipse 72, 74 is defined by its geometrical parameters. To minimize the number of required leg measurements, it is preferable to select a pair of ellipse-defining parameters which can uniquely define each ellipse 72 or 74. Such a preferred pair of ellipse-defining parameters is the length of the major axis and the length of the minor axis. Accordingly, measurements of the ellipse-defining parameters for each ellipse 72, 74 are obtained from the leg and synthesized with a measurement obtained from the leg for the longitudinal length L" between points 56" and 58" to define an elliptical cone 76" shown in partial outline. A cone 76 approximated in the manner described above with reference to FIG. 4A or FIG. 4B is shown superimposed over the upper leg 36' of a patient being prefitted with a leg brace in FIG. 3.

Figure 5:
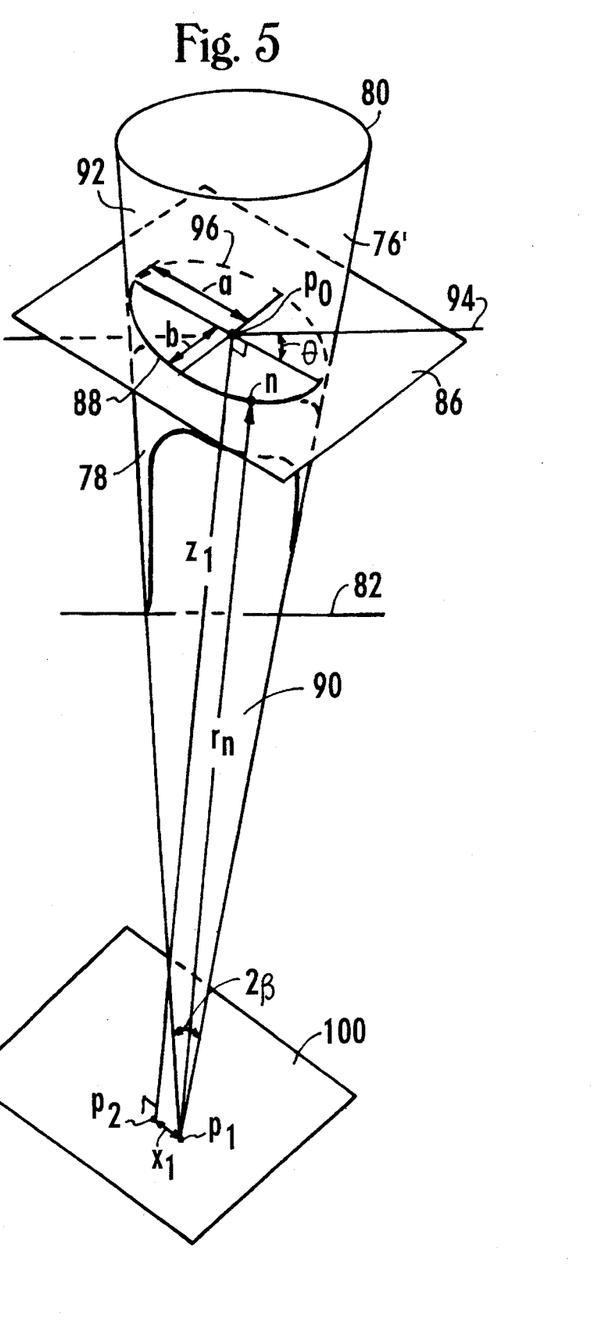
FIG. 5 is a perspective view of the conical surface of FIG. 3 having a three-dimensional pattern of an upper leg support member superimposed thereon.

FIG. 5 shows the circular cone 76' of FIG. 4A substantially in its entirety, having a three-dimensional pattern 78 for an upper leg support member of the type shown in FIG. 2 superimposed onto the conical surface 80 of the cone 76'. The pattern 78 occupies a modeling position on the conical surface 80 extending from above the knee to the knee joint pivot line 82, which corresponds to the placement position of the upper leg support member 52 on the upper leg 36 as shown in FIG. 2.

With the three-dimensional pattern 78 in the desired modeling position on the conical surface 80 of FIG. 5, the geometrical configuration and spatial dimensions of the pattern 78 are specified mathematically by applying analytical methods based on the defined geometry of the cone 76' and the relative positioning of the pattern 78 on the cone surface 80. Generation of the mathematical specifications for the pattern 78 can be expedited by machine-assisted analytical modeling of the cone 76' and pattern 78 using a conventional computer in accordance with the present method.

Figure 6:
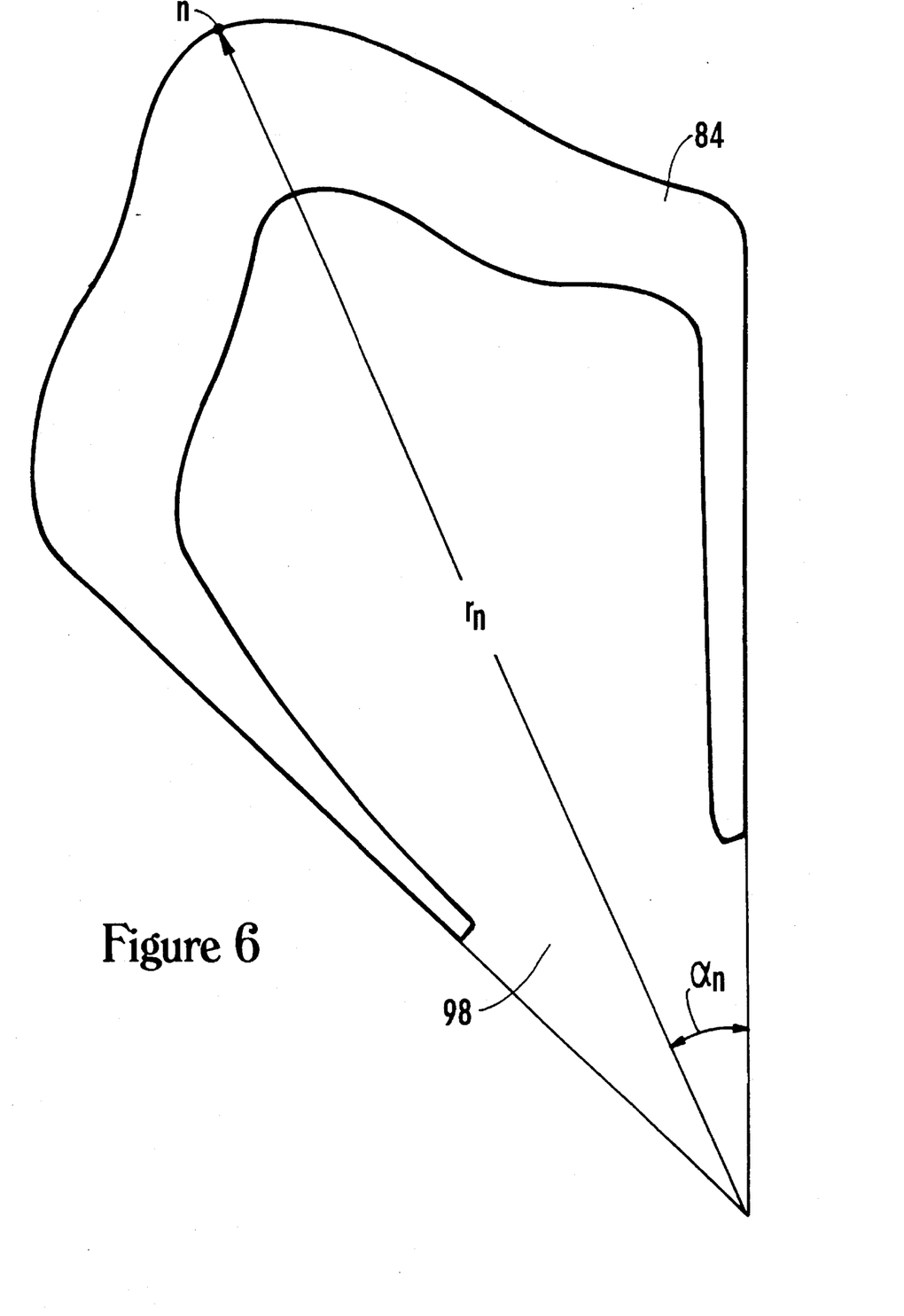
FIG. 6 is a two-dimensional mapping of the conical surface and pattern of FIG. 5.

In a preferred embodiment, the three-dimensional pattern 78 is mapped from the cone 76' onto a plane, thereby creating a two-dimensional mapping 84 of the pattern 78, as shown in FIG. 6 that facilitates generating the mathematical specifications of the pattern 78. The two-dimensional mapping 84 is created by slicing the cone 76' of FIG. 5 with a plane 86 passing therethrough containing the upper edge 88 of the three-dimensional pattern 78. Slicing the cone 76' produces an apex-containing portion 90 which retains the pattern 78 superimposed onto its surface 80. The remaining base-containing portion 92 of the cone has no further utility in the present method.

The apex-containing portion 90 of the cone is defined by angles $\beta$ and $\theta$, and a distance $r_n$, wherein $2\beta$=cone angle and $\theta$ is the angle between the horizontal 94 and the curve 96 resulting from the intersection of the conic portion 90 and the plane 86. $r_n$ is the distance from the apex point $P_o$ to any point n on the curve 96. A two-dimensional mapping 98 of the conic portion 90 shown in FIG. 6 is defined by $r_n$ and $\alpha_n$, wherein $\alpha_n$ is an angle having a range from 0 to $\pi(\sin\beta)$ and $r_n$ is the distance from the apex $P_o$ to the curve 96.

It is apparent with reference to FIG. 5 that if $\theta$=0, the curve 96 is simply a circle and $r_n$ is constant. Thus, the conic portion 90 is readily mapped in two dimensions at a constant r across the range of $\alpha_n$. However, if $\theta \neq 0$, the curve 96 is an ellipse and $r_n$ is variable. Thus, $r_n$ must be defined at each position of $\alpha_n$. The following equation is used to define $r_n$ across the entire range of $\alpha_n$, wherein $r_n$ represents the distance between the apex $P_o$ and any point n on the ellipse 96 obtained by slicing the circular cone 76' with the plane 86.

$$r_n = \left( \left( a\cos\left(\frac{\alpha_n}{\sin\beta}\right) - x_1 \right)^2 + \left( b\sin\left(\frac{\alpha_n}{\sin\beta}\right) - y_1 \right)^2 + z_1^2 \right)^{1/2}$$

$x_1$, $y_1$, and $z_1$ are constants establishing the position of the apex $p_1$ of the conic portion 90 within a new three-dimensional coordinate system defined by the ellipse 96, wherein the x-axis is aligned with the major axis of the ellipse 96, the y-axis is aligned with the minor axis of the ellipse, and the z-axis emanates from the center point $P_o$ of the ellipse 96 perpendicular to the plane 86 containing the ellipse 96.

The origin of the coordinate system defined by the ellipse 96 is the center point $P_o$ having coordinates $x_o$, $Y_o$, and $z_o$ all equal to zero. Accordingly, the apex $p_1$ of the conic portion 90 has coordinates $x_1$, $y_1$, and $z_1$, as shown in FIG. 5, wherein $z_1$ is the length of a perpendicular line segment from the center point $P_o$ to a plane 100 containing the apex $p_1$ that is parallel to the plane 86 containing the ellipse 96, $x_1$ is the distance of a line segment from the apex $p_1$ to the intersection point $P_2$ of the $z_1$ line segment and the plane 100, and for all circular cones, $y_1$= 0. a and b are constants related to the axes of the ellipse 96, wherein 2a=length of major axis and 2b=length of minor axis.

After the two-dimensional mapping 98 of the conic portion 90 is generated, this same equation can be used to generate the two-dimensional mapping 84 of the pattern 78 directly onto the mapping 98 or, alternatively, the three-dimensional pattern 78 can be mapped onto the two-dimensional mapping 98 by extrapolation from the known relationships between the three-dimensional pattern 78 and the three-dimensional portion 90 of the cone 76'. These tasks are expedited by performing the necessary computations using a conventional computer.

Once the mathematical specifications for either the three-dimensional pattern 78 or the two-dimensional mapping 84 of the pattern have been established, the desired upper leg support member 52 is fabricated in correspondence therewith, thus, providing an upper leg support member 52 that is prefitted to the contours of the upper leg 36. The three-dimensional support member 52 can be fabricated in three dimensions at the outset, or initially fabricated in two dimensions, and thereafter shaped into three dimensions.

It is understood that, although generation of the mathematical specifications for the pattern as described above are based on a circular cone, the specifications for the pattern could alternatively be generated in substantially the same manner based on an elliptical cone simply by modifying the algorithms, and applying them to an elliptical cone rather than a circular cone, as is readily apparent to the skilled artisan. The following example demonstrates the practice and utility of the present invention, but is not to be construed as limiting the scope thereof.

EXAMPLE

Two points on the left thigh of a patient to be prefitted with a knee brace are selected. The points are separated by a distance L=5 inches. A pair of circles are approximated by passing a pair of phantom cross-sectional planes containing the selected points through the thigh. The circles are determined to have a circumference of 16.14 inches and 20.00 inches, respectively. Using this data, a circular cone is constructed having a cone angle $2\beta=14°$.

A three-dimensional pattern for a thigh cuff is superimposed on the cone in a position corresponding to the desired position of the cuff on the thigh. The pattern is 2 inches high from the bottom edge to the parallely aligned top edge. The pattern is positioned on the cone such that the bottom edge intersects the larger of the two approximated circles at a medial point and deviates from the horizontal by an angle $\theta=10°$. Accordingly, the arc forming the top edge of the thigh cuff lies on a cutting plane through the cone defining an ellipse determined to have a major axis 2a=6,464 and a minor axis 2b=6.504. The pattern for the top edge of the thigh cuff is mapped in two dimensions across the range of angle $\alpha$, solving for r at each value of angle e according to the following equation after preliminary calculations are made to determine $x_1=4,599$, $y_1=0$, and $z_1=26.083$:

$$r_n = \left( \left( 3.232\cos\left( \frac{\alpha_n}{\sin 7°} \right) - 4.599 \right)^2 + \left( 3.252\sin\left( \frac{\alpha_n}{\sin 7°} \right) \right)^2 + 26.083^2 \right)^{1/2}$$

where:

$\alpha_n = 0 \rightarrow \pi(\sin 7°)$

A two-dimensional mapping of the bottom edge can be determined by plotting a parallel curve 2 inches from the two-dimensional mapping of the top edge to obtain a two-dimensional mapping of the entire cuff. A three-dimensional support member is then fabricated by shaping a two-dimensional form based on the two-dimensional mapping into three dimensions.

Although practice of the present method, as recited above, includes preliminarily obtaining a relatively small number of physical measurements of the desired body section being prefitted with the orthotic device, it is further within the scope of the present invention to practice the method by relying exclusively, or in part, on a statistical survey of body measurements from a population pool when prefitting a desired body section with an off-the-shelf orthotic device.

While the forgoing preferred embodiments of the invention have been described and shown, it is understood that alternatives and modifications, such as those suggested and others, may be made thereto and fall within the scope of the invention.

I claim:

1. A method for fabricating a stiffened orthotic support member of a hinged orthopedic brace having an approximated fit to a curved surface of a human body, said method comprising:

locating a desired placement position for a stiffened orthotic support member of a hinged orthopedic brace on a curved surface of a human body adjacent to a body joint to be supported by said brace;

selecting a first discrete point and a second discrete point on said curved surface of said human body, wherein said first and second discrete points are spaced a longitudinal distance apart;

selecting a first peripheral curve on said surface around said body containing said first discrete point;

selecting a second peripheral curve on said surface around said body containing said second discrete point;

modeling said curved surface of said body by defining a cone based on said longitudinal distance and said first and second peripheral curves, wherein said cone has a three-dimensional conical surface approximating said curved surface of said body;

superimposing a three-dimensional pattern onto a corresponding portion of said three-dimensional conical surface at a modeling position approximating said desired placement position; and fabricating said stiffened orthotic support member in correspondence with said three-dimensional pattern to approximate a fit of said orthotic support member to said curved surface of said human body.

2. A method as recited in claim 1, wherein said human body is a statistically modeled human body based on a population pool of human bodies.

3. A method as recited in claim 1, wherein said cone is an elliptical or circular cone.

4. A method as recited in claim 1, wherein said first peripheral curve lies on a first plane through said cone and said second peripheral curve lies on a second plane through said cone.

5. A method as recited in claim 4, further comprising:

defining a first circle lying on said first plane by determining a first circle-defining parameter, wherein said first circle approximates said first peripheral curve; and defining a second circle lying on said second plane by determining a second circle-defining parameter, wherein said second circle approximates said second peripheral curve.

6. A method as recited in claim 5, wherein said cone is defined based on said longitudinal distance and said first and second circle-defining parameters approximating said first and second peripheral curves, respectively.

7. A method as recited in claim 5, wherein said first and second circle-defining parameters are radii, diameters, or circumferences of said first and second circles, respectively.

8. A method as recited in claim 3, further comprising:

defining a first ellipse lying on said first plane by determining at least two first ellipse-defining parameters, wherein said first ellipse approximates said first peripheral curve; and defining a second ellipse lying on said second plane by determining at least two second ellipse-defining parameters, wherein said second ellipse approximates said second peripheral curve.

9. A method as recited in claim 8, wherein said cone is defined based on said longitudinal distance and said at least two first and second ellipse-defining parameters approximating said first and second peripheral curves, respectively.

10. A method as recited in claim 8, wherein said at least two first and second ellipse-defining parameters are major axes and minor axes of said first and second ellipses, respectively.

11. A method as recited in claim 1, further comprising transforming said three-dimensional conical surface to a corresponding two-dimensional surface on a two-dimensional coordinate system and superimposing a two-dimensional pattern corresponding to said three-dimensional pattern onto said two-dimensional surface.

12. A method as recited in claim 11, further comprising determining dimensional specifications in said two dimensional coordinate system of said two-dimensional pattern relative to said two-dimensional surface, wherein said dimensional specifications of said two-dimensional pattern correspond to dimensional specifications of said stiffened orthotic support member.

13. A method as recited in claim 1, further comprising determining dimensional specifications of said three-dimensional pattern relative to said three-dimensional conical surface, wherein said dimensional specifications of said three-dimensional pattern correspond to dimensional specifications of said stiffened orthotic support member.

14. A method as recited in claim 4, wherein said first plane is substantially parallel to said second plane.

15. A method as recited in claim 4, wherein said first and second planes are substantially cross-sectional to said body.

16. A method for fabricating a stiffened orthotic support member of a hinged orthopedic brace having an approximated fit to a curved surface of a human body, said method comprising:

locating a desired placement position for a stiffened orthotic support member of a hinged orthopedic brace on a curved surface of a human body adjacent to a body joint to be supported by said brace;

modeling said curved surface of said body by defining a cone having a three-dimensional conical surface approximating said curved surface of said human body;

superimposing a three-dimensional pattern onto a corresponding portion of said three-dimensional conical surface at a modeling position approximating said desired placement position; and fabricating said stiffened orthotic support member in correspondence with said three-dimensional pattern to approximate a fit of said orthotic support member to said curved surface of said human body.

17. A method as recited in claim 16, further comprising transforming said three-dimensional conical surface to a corresponding two-dimensional surface on a two-dimensional coordinate system and superimposing a two-dimensional pattern corresponding to said three-dimensional pattern onto said two-dimensional surface.

18. A method as recited in claim 17, further comprising determining dimensional specifications in said two dimensional coordinate system of said two-dimensional pattern relative to said two-dimensional surface, wherein said dimensional specifications of said two-dimensional pattern correspond to dimensional specifications of said stiffened orthotic support member.

19. A method as recited in claim 16, further comprising determining dimensional specifications of said three-dimensional pattern relative to said three-dimensional conical surface, wherein said dimensional specifications of said three-dimensional pattern correspond to dimensional specifications of said stiffened orthotic support member.

20. A method for prefitting a stiffened orthopedic support member to a curved surface on the body of a human subject comprising:

locating a desired placement position for a stiffened orthotic support member on a curved surface of a human body;

selecting a first point on a first peripheral curve around said curved surface of said human body, said first peripheral curve defining a first plane;

selecting a second point on a second peripheral curve around said curved surface, said second point spaced a longitudinal distance apart from said first point and said second peripheral curve defining a second plane;

approximating a first circle from said first peripheral curve;

approximating a second circle from said second peripheral curve;

defining a conical surface based on said longitudinal distance and said first and second circles, wherein said conical surface approximates said curved surface of said body;

superimposing a pattern on said conical surface at a modeling position, wherein said modeling position of said pattern corresponds to said desired placement position;

specifying dimensions of said stiffened orthotic support member in correspondence to said pattern; and fabricating said stiffened orthotic support member in correspondence with said dimensions to prefit said curved surface of said human body.

21. A method as recited in claim 20, wherein said conical surface and said pattern are defined in a three-dimensional coordinate system.

22. A method as recited in claim 20, further comprising generating a two-dimensional mapping of said pattern wherein said dimensions of said member correspond to said two-dimensional mapping.

23. A method for fabricating a stiffened orthotic support member prefitted to a curved surface of a human body comprising:

locating a desired placement position for a stiffened orthotic support member on a curved surface of a human body;

selecting a first point on a first peripheral curve around said curved surface of said human body, said first peripheral curve defining a first plane;

selecting a second point on a second peripheral curve around said curved surface, said second point spaced a longitudinal distance apart from said first point and said second peripheral curve defining a second plane;

approximating a first ellipse from said first peripheral curve;

approximating a second ellipse from said second peripheral curve;

defining a conical surface based on said longitudinal distance and said first and second ellipses, wherein said conical surface approximates said curved surface of said body;

superimposing a pattern on said conical surface at a modeling position, wherein said modeling position of said pattern corresponds to said desired placement position;

specifying dimensions of said stiffened orthotic support member in correspondence to said pattern; and fabricating said stiffened orthotic support member in correspondence with said dimensions to prefit said curved surface of said human body.

24. A method as recited in claim 23, wherein said conical surface and said pattern are defined in a three-dimensional coordinate system.

25. A method as recited in claim 23, further comprising generating a two-dimensional mapping of said pattern wherein said dimensions of said member correspond to said two-dimensional mapping.

* * * * *